United States Patent [19]

Tsai

[11] Patent Number: 5,480,647
[45] Date of Patent: Jan. 2, 1996

[54] FAR-INFRARED RADIATING MEDICAL COMPOUND AND AN ADHESIVE SURGICAL TAPE LAYERING THE COMPOUND

[75] Inventor: Chung Y. Tsai, Taipei, Taiwan

[73] Assignee: Fu Hsiang Textile Co., Ltd., Taipei, Taiwan

[21] Appl. No.: 325,926

[22] Filed: Oct. 18, 1994

[51] Int. Cl.⁶ .................................................. A61K 9/00
[52] U.S. Cl. ...................... 424/443; 424/447; 424/448; 424/449; 602/41; 602/58; 602/903; 604/304; 604/307
[58] Field of Search ............................ 424/443, 447, 424/448, 449

[56] References Cited

U.S. PATENT DOCUMENTS

| | | | |
|---|---|---|---|
| 4,222,923 | 9/1980 | Rhodes et al. | 128/275 |
| 4,795,536 | 1/1989 | Young et al. | 204/129 |
| 5,225,199 | 7/1993 | Hidaka et al. | 424/443 |

FOREIGN PATENT DOCUMENTS

| | | |
|---|---|---|
| 40-21557 | 9/1965 | Japan . |
| 62-057605 | of 1985 | Japan . |

*Primary Examiner*—Thurman K. Page
*Assistant Examiner*—Pamela S. Webber
*Attorney, Agent, or Firm*—Beveridge, DeGrandi, Weilacher, Young

[57] ABSTRACT

Provided is a medical compound and a surgical tape containing the medical compound for curing muscle ache and stiffness. The medical compound is capable of radiating farinfrared in the wavelength rang of 3–16 μm when stimulated by body heat. It has the effects of vitalizing cells and promoting metabolism. The medical compound is composed of powdered perelite and at least one metallic oxide such as $Ta_2O_5$, $Nb_2O_5$, NiO and the like, which will not cause environmental pollution when the surgical tape is discarded after use.

7 Claims, No Drawings

FAR-INFRARED RADIATING MEDICAL COMPOUND AND AN ADHESIVE SURGICAL TAPE LAYERING THE COMPOUND

FIELD OF THE INVENTION

The present invention relates to medical articles, and more particularly, to a surgical tape layering a far-infrared radiating medical compound for curing muscle ache and stiffness.

BACKGROUND OF THE INVENTION

One traditional method for curing muscle ache and stiffness is to bathe spa, which can be found near volcanic sites. The molten rock, or lava, issued from a volcano usually emits radiation in the wavelength range of 6–12 μm, which lies in the spectrum of far-infrared. The spa is fed by underground water heated by the lava, so it also contains the far-infrared radiation. The spa is very effective in curing muscle ache and stiffness but it is also a costly method.

In addition to the spa, many surgical tapes are available for use in curing muscle ache and stiffness. These surgical tapes can be adhered conveniently and easily to the skin.

However, one drawback of the prior art surgical tapes is that they use medicines that may cause environmental pollution when discarded after use. Another drawback is that these surgical tapes often have a limited period of effectiveness.

A medical research paper entitled "The Effects of Porcelain-emitted Far-infrared Radiation on the Vitalization of Lymphocyte" and disclosed by a Japanese research center has proven that far-infrared radiation can vitalize human cells. In the research, it is found that several kinds of porcelain emit far-infrared radiation when heated. The radiation affects the human body in several aspects. For example, it raises the temperature in the inner layer of the skin, expands the capillaries, ameliorates blood circulation, promotes metabolism, relaxes the sensory nerves, and regulates the autonomic nerve system.

Through research on far-infrared emitting porcelains, the inventor has found that a compound made from one kind of volcanic rock called perlite can be used to cure muscle ache and stiffness. The perlite rock is powdered and sintered at 1100°–1300° C. and then mixed with at least one metallic oxide of which the metal is selected from the group consisting of Ta, Nb, Pd, Ni, Ge, Ti and Zr of specific proportions. When layered on a tape and adhered to the muscle, this compound can emit far-infrared radiation when it comes in contact with the body heat. The amount of radiation can expand the capillaries 1.3 to 1.4 time.

SUMMARY OF THE INVENTION

It is a primary objective of the present invention to provide a surgical tape that provides curing effect to muscle ache and stiffness.

It is another objective of the present invention to provide a surgical tape that provides no pollution to the environment when it is discarded after use.

It is a further objective of the present invention to provide a surgical tape that facilitates blood circulation such that the body cell can be activated, the aging process can be retarded and the healthy condition can be improved.

In accordance with the above and other objectives, the present invention provides a medical compound capable of radiating far-infrared in the wavelength range of 34–16 μm when stimulated by body heat. The medical compound is composed of 70 wt %–90 wt % of powdered perlite and 10 wt %–30 wt % of at least one metallic oxide of which the metal is selected from the group consisting of Ta, Nb, Pd, Ni, Ge, Ti and Zr. The composition of the perlite includes 73.41% of $SiO_2$, 12.34% of $Al_2O_3$, 1.33% $Fe_2O_3$, 2.95% $Na_2O$, 5.33% $K_2O$, and 3.70% of crystallized water.

The present invention also provides a surgical tape which contains a layer of the above-mentioned medical compound.

DETAILED DESCRIPTION OF THE PREFERRED EMBODIMENTS

Perlite is a kind of volcanic rock composed of 73.41% of $SiO_2$, 12.34% of $Al_2O_3$, 1.33% $Fe_2O_3$, 2.95 $Na_2O$, 5.33% $K_2O$, and 3.70% of crystallized water. It is commonly used as construction material, sound-absorbing plate, filtering agent, and fill.

The perlite used by the present invention is powdered and sintered at 1100°–1300° C. for 3–8 hours. It has a purity of more than 99.9% and a granularity of 7–8μm. Heated by low temperature such as that from the body's heat, the powder emits far-infrared radiation in the wavelength range of 3–16μm.

The amount of radiation can be significantly increased when the powdered perlite is mixed with at least one powdered metallic oxide of which the metal is selected from the group consisting of Ta, Nb, Pd, Ni, Ge, Ti and Zr in specific proportions. These additives have a purity of more than 99.99% and a granularity of 17–20μm.

The medical compound of the present invention is composed of 70 wt %–90 wt % of powdered perlite and 10 wt %–30 wt % of at least one metallic oxide of which the metal is selected from the group consisting of Ta, Nb, Pd, Ni, Ge, Ti and Zr. This compound can emit far-infrared radiation in the wavelength range of 3–16μm when it comes in contact with body heat. The radiation in this wavelength range provides strong heat-resonance effect to the skin, thereby generating heat that vitalizes the activity of cells, expands the capillaries, and promotes metabolism.

To conveniently apply the medical compound of the present invention to the skin an adhesive surgical tape is used. The surgical tape may be mounted with a flat bag or a fibrous material used to contain the medical compound of the present invention. To use the compound, users can simply adhere the surgical tape to the skin where ache or stiffness occurs.

Compared with prior art surgical tape, the present invention provides several advantages. First, the composition will provide no pollution to the environment when it is discarded as a waste after use. Second, the medical compound of the present invention can be used continuously, having no limited period of effectiveness. And third, it provides better curing effect as evidenced by the following clinical cases.

CLINICAL EXPERIMENTS

Two surgical tapes, one being made according to the present invention and one being prior art, are used by the same patient in different parts of the body.
Case 1:

A 60-year-old male patient suffered from ache and stiffness in the shoulder and back. The surgical tape of the present invention was adhered to his shoulder and the prior art one was adhered to his back. After two days of use, the ache and stiffness in the shoulder was completely relieved while that in the back was only slightly alleviated.

Case 2:

A 42-year-old female patient was injured in the hip from an accident. After being treated, however, the hip still suffered from ache when the weather turned cold. The prior art surgical tape was adhered to her hip first. After three hours of se, the ache still existed. The surgical tape of the present invention was then substituted. After two hours of use, the ache began to subside; and after two more hours, the ache was completely gone.

Case 3:

A 35-year-old female patient frequently suffered from insomnia. The prior art surgical tape was adhered to her ankle first for two consecutive days. She still suffered from the insomnia. After three days, the surgical tape of the present invention was adhered to her ankle in substitution. In the first night, the lady slept two more hours than before. After one week of continuous use, the lady was able to sleep for six hours each night.

Case 4:

A 55-year-old male patient suffered from an ache in the joint of the hand. After four days of use of the prior art surgical tape, the ache was only slightly alleviated. After two days, the surgical tape of the present invention was adhered in substitute. After two days of use, he felt more comfortable with the hand and after three more days of use, the ache was completely relieved and he could use his hand freely.

What is claimed is:

1. A medical compound comprising: 70 wt %–90 wt % of powdered perlite and 10 wt %–30 wt % of at least one metallic oxide of which the metal is selected from the group of tantalum, niobium, palladium, nickel, germanium, titanium, and zirconium.

2. A medical compound as claimed in claim 1, wherein said powdered perlite has been sintered at a temperature in the range of 1100°–1300° C. for a period in the range of 3–8 hours.

3. A medical compound as claimed in claim 1, wherein said powdered perlite is composed of 73.41% of $SiO_2$, 12.34% of $Al_2O_3$, 1.33% of $Fe_2O_3$, 2.95% of $Na_2O$, 5.33% of $K_2O$, and 3.70% of crystallized water.

4. A medical compound as claimed in claim 2, wherein said powdered perlite has a purity of more than 99.9% and a granularity in the range of 7–8μm.

5. A medical compound as claimed in claim 2, wherein said metallic oxide has a purity of 99.99% and a granularity in the range of 17–20μm.

6. A surgical tape containing the medical compound as claimed in claim 1.

7. A surgical tape as claimed in claim 6, wherein the medical compound is mixed with fibrous material.

* * * * *